United States Patent [19]
Dyke et al.

[11] Patent Number: 5,773,467
[45] Date of Patent: Jun. 30, 1998

[54] BENZOFURAN SULPHONANMIDES

[75] Inventors: Hazel Joan Dyke; Hannah Jayne Kendall; Christopher Lowe; John Gary Montana, all of Cambridge, United Kingdom

[73] Assignee: Chiroscience, Ltd., Cambridge, United Kingdom

[21] Appl. No.: 761,102

[22] Filed: Dec. 5, 1996

[30] Foreign Application Priority Data

Dec. 5, 1995 [GB] United Kingdom .................... 9524832
May 20, 1996 [GB] United Kingdom .................... 9610515
May 22, 1996 [GB] United Kingdom .................... 9610712

[51] Int. Cl.⁶ .................... A61K 31/34; C07D 307/86; C07D 307/78
[52] U.S. Cl. .................... 514/469; 546/282.7; 549/467; 549/468; 549/469; 549/471
[58] Field of Search .................... 549/471, 468, 549/467, 469; 546/282.7; 514/469

[56] References Cited

FOREIGN PATENT DOCUMENTS

| | | |
|---|---|---|
| 0187387 | 7/1986 | European Pat. Off. . |
| 0685475 | 12/1995 | European Pat. Off. . |
| 771794 | 5/1997 | European Pat. Off. . |
| 96 03399 | 7/1995 | WIPO . |

*Primary Examiner*—Bernard Dentz
*Attorney, Agent, or Firm*—Saliwanchik, Lloyd & Saliwanchik

[57] ABSTRACT

Benzofuran carboxides and sulphonamides have therapeutic utility, e.g. in the treatment of inflammation and asthma, by virtue of their ability to inhibit phosphodiesterases and tumor necrosis factor.

25 Claims, No Drawings

5,773,467

BENZOFURAN SULPHONANMIDES

FIELD OF THE INVENTION

The present invention relates to novel benzofuran carboxamides and sulphonamides, and to their formulation and use as pharmaceuticals.

BACKGROUND OF THE INVENTION

EP-A-0187387 discloses benzofuransulphonamides having aldose reductase, platelet aggregation and arachidonic acid metabolism inhibitory activity.

U.S. Pat. No. 4,910,193 discloses benzofuransulphonamides, in which the sulphonamide nitrogen is substituted by a variety of bridged saturated ring systems, as medicaments suitable for the treatment of serotonin-induced gastrointestinal disturbances.

EP-A-0637586 discloses benzofuran derivatives, including 4-carboxamides, as acetylcholine esterase inhibitors.

WO-A-9408962 discloses benzofuran analogues as fibrinogen receptor antagonists.

WO-A-9203427 discloses benzofuran-2-carboxamides, with a 3-substituent selected from hydroxy, acyloxy, alkoxy, optionally alkyl-substituted aminoalkoxy, alkylsulphonylamino, optionally alkyl-substituted aminoalkylsulphonyl or arylsulphonylamino, as a remedy for osteoporosis.

EP-A-0685475 discloses benzofuran-2 carboxamides as anti-inflammatory agents.

WO-A-9603399 discloses dihydrobenzofuran-4-carboxamides as inhibitors of phosphodiesterases.

Phosphodiesterases (PDE) and Tumour Necrosis Factor (TNF), their modes of action and the therapeutic utilities of inhibitors thereof, are described in WO-A-9636595, WO-A-9636596 and WO-A-9636611, the contents of which are incorporated herein by reference. The same documents disclose sulphonamides having utility as PDE and TNF inhibitors.

SUMMARY OF THE INVENTION

This invention is based on the discovery of novel compounds that can be used to treat disease states, for example disease states associated with proteins that mediate cellular activity, for example by inhibiting tumour necrosis factor and/or by inhibiting phosphodiesterase IV. According to the invention, the novel compounds are of formula (i):

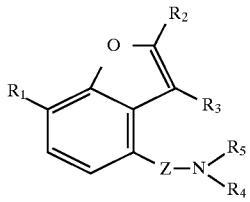

wherein Z is $SO_2$, CO or CS;

$R_1$ represents alkoxy optionally substituted with one or more halogens, OH or thioalkyl;

$R_2$ and $R_3$ are the same or different and are each H, $R_6$, $COR_6$, $C(=NOR_{11})R_6$, CN, $CO_2H$, $CO_2R_{10}$, $CONH_2$, $CONHR_6$ or $CON(R_6)_2$;

$R_4$ represents H, arylalkyl, heteroarylalkyl, heterocycloalkyl, $S(O)_mR_{10}$ or alkyl optionally substituted with one or more substituents chosen from hydroxy, alkoxy, $CO_2R_7$, $SO_2NR_{11}R_{12}$, $CONR_{11}R_{12}$, CN, carbonyl oxygen, $NR_8R_9$, $COR_{10}$ and $S(O)_nR_{10}$;

$R_5$ represents aryl, heteroaryl, heterocyclo, arylalkyl, heteroarylalkyl or heterocycloalkyl;

in $R_4$ and/or $R_5$, the aryl/heteroaryl/heterocyclo portion is optionally substituted with one or more substituents alkyl-$R_{13}$ or $R_{13}$;

$R_6$ represents $R_{10}$ optionally substituted at any position with (one or more) $R_{14}$;

$R_7$ represents H, alkyl, arylalkyl, hetarylalkyl or heterocycloalkyl;

$R_8$ represents H, aryl, heteroaryl, heterocyclo, alkyl, arylalkyl, heteroarylalkyl, heterocycloalkyl, alkylcarbonyl, alkoxycarbonyl, arylsulphonyl, heteroarylsulphonyl, heterocyclosulphonyl, arylcarbonyl, heteroarylcarbonyl, heterocyclocarbonyl or alkylsulphonyl;

$R_{10}$ represents alkyl, cycloalkyl, aryl, heteroaryl, heterocyclo, arylalkyl, heteroarylalkyl or heterocycloalkyl;

$R_9$, $R_{11}$ and $R_{12}$ are the same or different, and are each H or $R_{10}$;

$R_{13}$ represents alkyl or alkoxy optionally substituted by halogen, aryl, heteroaryl, heterocyclo, hydroxy, aryloxy, heteroaryloxy, heterocyclooxy, arylalkyloxy, heteroarylalkyloxy, heterocycloalkyloxy, $CO_2R_7$, $CONR_{11}R_{12}$, $SO_2NR_{11}R_{12}$, halogen, —CN, —$NR_8R_9$, $COR_{10}$, $S(O)_nR_{10}$, or carbonyl oxygen;

$R_{14}$ represents OH, $OR_{10}$, carbonyl oxygen, $NR_8R_9$, CN, $CO_2H$, $CO_2R_{10}$, $CONR_{11}R_{12}$ or $COR_{10}$;

m represents 1–2; and n represents 0–2;

and pharmaceutically-acceptable salts.

Combinations of substituents and/or variables are only permissible if such combinations result in stable compounds.

DESCRIPTION OF THE INVENTION

Suitable pharmaceutically-acceptable salts are pharmaceutically-acceptable base salts and pharmaceutically-acceptable acid addition salts. Certain of the compounds of formula (i) which contain an acidic group form base salts. Suitable pharmaceutically-acceptable base salts include metal salts, such as alkali metal salts for example sodium salts, or organic amine salts such as that provided with ethylenediamine.

Certain of the compounds of formula (i) which contain an amino group form acid addition salts. Suitable acid addition salts include pharmaceutically-acceptable inorganic salts such as the sulphate, nitrate, phosphate, borate, hydrochloride and hydrobromide and pharmaceutically-acceptable organic acid addition salts such as acetate, tartrate, maleate, citrate, succinate, benzoate, ascorbate, methanesulphate, α-ketoglutarate, α-glycerophosphate and glucose-1-phosphate. The pharmaceutically-acceptable salts of the compounds of formula (i) are prepared using conventional procedures.

It will be appreciated by those skilled in the art that some of the compounds of formula (i) may exist in more than one tautomeric form. This invention extends to all tautomeric forms.

It will be appreciated that the compounds according to the invention can contain one or more asymmetrically substituted atoms. The presence of one or more of these asymmetric centers in a compound of formula (i) can give rise to stereoisomers, and in each case the invention is to be understood to extend to all such stereoisomers, including enantiomers, and diastereoisomers and mixtures including racemic mixtures thereof.

When used herein the term alkyl whether used alone or when used as a part of anther group includes straight and branched chain alkyl groups containing up to 6 atoms. Alkoxy means an alkyl-O— group in which the alkyl group is as previously described. Aryloxy means an aryl-O— group in which the aryl group is as defined below. Heteroaryloxy means a heteroaryl-O— group and heterocyclooxy means a heteroyclo-O— group in which the heteroaryl and heterocyclo group are as defined below. Arylalkyloxy means an aryl-alkyl-O— group. Heteroarylalkyloxy means a heteroaryl-alkyl-O group and heterocycloalkyloxy means a heterocyclo-alkyl-O— group. Aryloxyalkyl means an aryl-O-alkyl group, heteroaryloxyalkyl means a heteroaryl-O-alkyl group and heterocyclooxyxlkyl means a heterocyclo-O-alkyl group. Alkylamino means an alkyl-N- group in which the alkyl group is as previously defined, arylamino mans aryl-N- and heteroarylamino means an heteroaryl-N- group (aryl and heteroaryl defined below). Thioalkyl means an alkyl-S-group. Cycloalkyl includes a non-aromatic cyclic or multicyclic ring system of about 3 to 10 carbon atoms. The cyclic alkyl may optionally be partially unsaturated. Aryl indicates carbocyclic radicals containing about 6 to 10 carbon atoms. Arylalkyl means an aryl-alkyl- group wherein the aryl and alkyl are as described herein, Heteroarylalkyl means a heteroaryl-alkyl group and heterocycloalkyl means a heterocycloalkyl group. Alkylcarbonyl means an alkyl-CO— group in which the alkyl group is as previously described. Arylcarbonyl means an aryl-CO— group in which the aryl group is as previously described. Heteroarylcarbonyl means a heteroaryl-CO— group and heterocyclocarbonyl means a heterocyclo-CO— group. Arylsulphonyl means an aryl-SO$_2$— group in which the aryl group is as previously described. Heteroarylsulphonyl means a heteroaryl-SO$_2$— group and heterocyclosulponyl means a heterocyclo-SO$_2$— group. Alkoxycarbonyl means an alkyloxy-CO— group in wich the alkoxy group is as previously described. Alkylsulphonyl means an alkyl-SO$_2$— group in which the alkyl group is as previously described. Carbonyl oxygen means a —CO— group, it will be appreciated that a carbonyl oxygen can not be a substituent on an aryl or heteroaryl ring. Carbocyclic ring means about a 5 to about a 10 membered monocyclic or multicyclic ring system which may saturated or partially unsaturated. Heterocyclic ring means about a 5 to about a 10 membered monocyclic or multicyclic ring system (which may saturated or partially unsaturated) wherein one or more of the atoms in the ring system is an element other than carbon chosen from amongst nitrogen, oxygen or sulphur atoms. Heteroaryl means about a 5 to about a 10 membered aromatic monocyclic or multicyclic hydrocarbon ring system in which one or more of the atoms in the ring system is an element other than a chosen from amongst nitrogen, oxygen or sulphur. Heterocyclo means about a 5 to about a 10 membered saturated or partially saturated monocyclic or multicyclic hydrocarbon ring system in which one or more of the atoms in the ring system is an clement other than carbon, chosen from amongst nitrogen, oxygen or sulphur. Halogen means fluorine, chlorine, bromine or iodine.

Compounds of the invention art useful for the treatment of TNF mediated disease states. "TNF mediated disease or disease states" means any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by compounds of the present invention and thus are herein referred to collectively as "TNF" unless specifically indicated otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically-acceptable salt thereof.

PDE IV inhibitors are useful in the treatment of a variety of allergic and inflammatory diseases, including: asthma, chronic bronchitis, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, sepsis, ulcerative colitis, Crohn's disease, reperfusion injury of the myocardium and brain, chronic glomerulonephritis, endotoxic shock and adult respiratory distress syndrome, In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia, PDE IV inhibitors are also useful in conditions ameliorated by neuroprotectant activity, such as cardiac arrest, stroke and intermittent claudication. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes simplex.*

This invention more specifically relates to a method of treating a mammal, afflicted with a human immunodeficiency virus (HIV), which comprises administering to such mammal an effective TNF inhibiting amount of a compound of Formula (i) or a pharmaceutically-acceptable salt thereof.

The compounds of this invention may be also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

Compounds of the invention may also suppress neurogenic inflammation through elevation of cAMP in sensory neurones. They are, therefore, analgesic, anti-tussive and anti-hyperalgesic in inflammatory diseases associated with irritation and pain.

The compounds of formula (i) are preferably in pharmaceutically-acceptable form. By pharmaceutically-acceptable form is meant, inter alia, of a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%.

The invention further provides a process for the preparation of a compound of formula (i), in which $R_1$ etc, m and n are as defined above. It will be appreciated that functional groups such as amino, hydroxyl or carboxyl groups present in the various compounds described below, and which it is desired to retain, may need to be in protected forms before any reaction is initiated. In such instances, removal of the protecting group may be the final step in a particular reaction. Suitable protecting groups for such functionality will be apparent to those skilled in the art. For specific details, see Protective Groups in Organic Synthesis, Wiley Interscience, TW Greene. Thus the process for preparing compounds of formula (i) in which $R_4$ contains an —OH comprises of deprotecting (for example by hydrogenolysis or hydrolysis) a compound of formula (i) in which $R_4$ contains an appropriate —OP wherein P represents a suitable protecting group (e.g. benzyl).

It will be appreciated that where a particular stereoisomer of formula (i) is required, this may be obtained by conventional resolution techniques such as high performance liquid chromatography or the synthetic processes herein described may by performed using the appropriate homochiral starting material.

A process for the preparation of a compound of formula (i) wherein Z is $SO_2$ comprises reaction of an appropriate sulphonyl chloride of formula (ii) with a suitable amine of formula (iii)

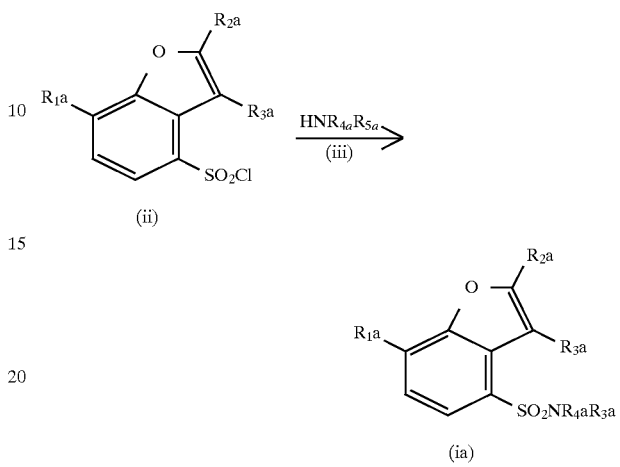

wherein $R_{1a}$ represents $R_1$ as defined in relation to formula (i) or a group convertible to $R_1$ and $R_{2a}$—$R_{5a}$ similarly represent $R_2$—$R_5$ or groups convertible to $R_2$—$R_5$ respectively; and thereafter, if required, converting any group $R_{1a}$ to $R_1$ and/or $R_{2a}$ to $R_2$ and/or $R_{3a}$ to $R_3$ and/or $R_{4a}$ to $R_4$ and/or $R_{5a}$ to $R_5$. The reaction of a sulphonyl chloride of formula (ii) with an amine of formula (iii) may be carried out under any suitable conditions known to those skilled in the art. Favourably, the reaction is carried out in the presence of a suitable base, for example an amine such as triethylamine, preferably in an appropriate solvent such as dichloromethane. In some cases a stronger base, such as sodium hydride, and a polar solvent such as dimethylformamide, will be required.

Sulphonyl chlorides of formula (ii) and amines (iii) are either commercially available, previously described compounds or are prepared using standard procedures known to those skilled in the art. Some of the amines of formula (iii) are conveniently prepared by reductive amination of an appropriate carbonyl compound with a suitable amine. This amination may be carried out under any suitable standard conditions known to those skilled in the art.

For example, a sulphonyl chloride of formula (ii) is conveniently prepared from the appropriate sulphonic acid (iv) by treatment with a suitable agent such as thionyl chloride or oxalyl chloride. Alternatively, a sulphonyl chloride of formula (ii) may be prepared by sulphonylation of an appropriate benzofuran of formula (v) with a suitable sulphonylating agent such as chlorosulphonic acid.

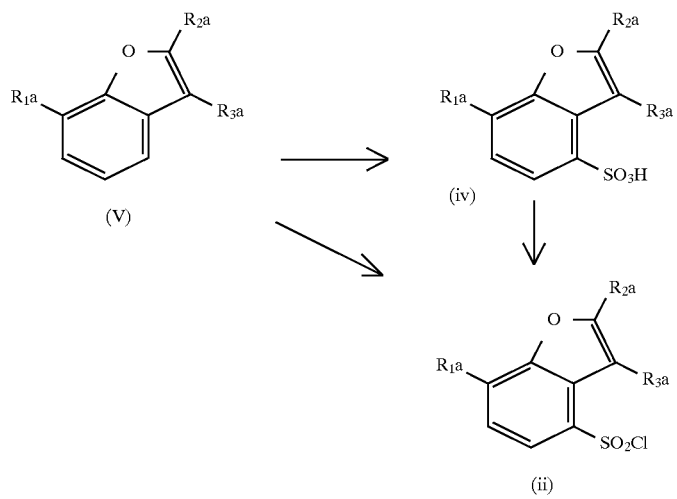

Benzofurans of formula (v) may be prepared by any standard procedure known to those skilled in the art, for example by the reaction between an appropriate 2-hydroxybenzaldehyde or 2-hydroxyphenyl ketone (vi) and a suitable alkylating agent (vii) in the presence of an appropriate base (such as potassium carbonate or sodium hydroxide) in a suitable solvent (such as dimethylformamide or ethanol) at an appropriate temperature (for example reflux temperature of the solvent).

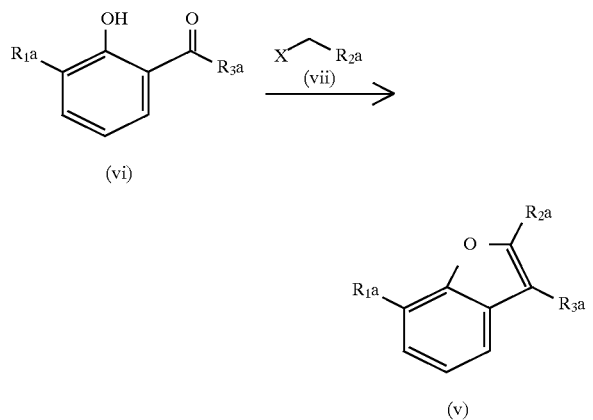

Examples of suitable alkylating agents include chloroacetone and chloroacetonitrile. Compounds (vi) and suitable alkylating agents (vii) are commercially available, previously described compounds or may be prepared by standard procedures known to those skilled in the art.

A compound of formula (ia) may also be prepared by reaction of a sulphonyl chloride of formula (ii) with an amine of formula $H_2NR_{5a}$ (viii) to provide a compound of formula (ia) in which $R_{4a}$ is H, followed by reaction with an appropriate agent of formula $R_{4a}Y$ (ix) in which Y is a suitable leaving group such as a halogen. The reaction of a sulphonyl chloride of formula (ii) with an amine of formula (viii) may be carried out under any suitable conditions known to those skilled in the art. Favourably, the reaction is carried out in the presence of a suitable base, for example an amine such as triethylamine, preferably in an appropriate solvent such as dichloromethane. In some cases a stronger base such as sodium hydride, and a polar solvent such as dimethylformamide, may be required.

Amines of formula (viii) and agents (ix) are either commercially available, previously described compounds or are prepared using standard procedures known to those skilled in the art. The reaction of a compound of formula (ia) in which $R_4$ is H with an agent of formula (ix) may be carried out under any suitable conditions known to those skilled in the art. Favourably, the reaction is carried out using an appropriate base, such as sodium hydride, preferably in an appropriate solvent such as dimethylformamide. Agent (ix) can be an alkylating agent such as propyl bromide, an acylating agent such as benzoyl chloride or a sulphonylating agent such as methanesulphonyl chloride.

A process for the preparation of a compound of formula (i) wherein Z is CO comprises reaction of an appropriate carboxylic acid of formula (x) with a suitable amine of formula (iii)

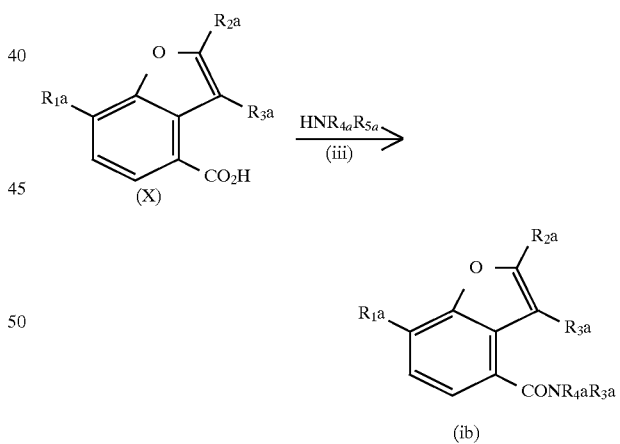

wherein $R_{1a}$ etc are as defined above; and thereafter, if required, converting any group $R_{1a}$ to $R_1$ and/or $R_{2a}$ to $R_2$ and/or $R_{3a}$ to $R_3$ and/or $R_{4a}$ to $R_4$ and/or $R_{5a}$ to $R_5$. The reaction of a carboxylic acid of formula (x) with an amine of formula (iii) may be carried out under any suitable conditions known to those skilled in the art, preferably those described above for (ii)→(ia). Favourably, the carboxylic acid is converted into an acid chloride, mixed anhydride or other activated intermediate prior to reaction with an amine of formula (iii).

Carboxylic acids of formula (x) are either commercially available, previously described compounds or are prepared using standard procedures known to those skilled in the art. For example, a carboxylic acid of formula (x) is conveniently prepared from an appropriate benzofuran of formula (v), using standard procedures known to those skilled in the art. For example, a benzofuran of formula (v) can be formylated to provide an aldehyde of formula (xi), which can then be oxidised to provide the corresponding acid of formula (x). Alternatively, a benzofuran of formula (v) can be brominated to provide a bromide of formula (xii), which can then be converted into a carboxylic acid of formula (x), for example by organometal-catalysed carboxylation.

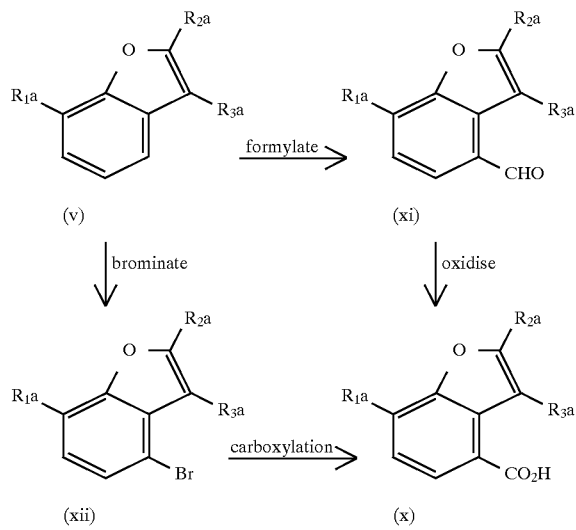

A compound of formula (ib) may also be prepared by reaction of a carboxylic acid of formula (x) with an amine (viii) to provide a compound of formula (ib) in which $R_{4a}$ is H, followed by reaction with an agent (ix). These reactions, with amine (viii) and agent (ix), can be carried out as described above. Preferably, the carboxylic acid is converted into an acid chloride, mixed anhydride or other activated intermediate prior to reaction with the amine (viii).

Compounds of formula (i) may also be prepared by interconversion of other compounds of formula (i). For example, a compound in which $R_4$ contains an alkoxy group may be prepared by appropriate alkylation of a compound in which $R_4$ contains a hydroxy group.

By way of further example, compounds in which $R_2$ and/or $R_3$ contain an oxime may be prepared from compounds in which $R_2$ and/or $R_3$ contain a carbonyl group. This transformation may be carried out using any appropriate standard conditions known to those skilled in the art. Compounds of formula (i) in which $R_2$ and/or $R_3$ contain a carbonyl group may be reduced using standard conditions known to those skilled in the art (for example with sodium borohydride in an appropriate solvent) to provide compounds in which $R_2$ and/or $R_3$ contains an alcohol group. Compounds in which $R_2$ and/or $R_3$ is alkyl may be prepared by reduction of compounds in which $R_2$ and/or $R_3$ is CO-alkyl using standard conditions known to those skilled in the art (for example hydrazine hydrate in the presence of a suitable base in an appropriate solvent). Other transformations may be carried out on compounds of formula (i) in which $R_2$ and/or $R_3$ contains a carbonyl group. Such transformations include, but are not limited to, reductive amination and alkylation. Any of the above transformations may be carried out either at the end of the synthesis or on an appropriate intermediate. Compounds of formula (i) in which Z is CS may be prepared from compounds of formula (i) in which Z is CO using any appropriate conditions known to those skilled in the art, for example by using Lawesson's reagent.

A compound of formula (i) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion tecniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically-acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 $\mu$m, such as from 0.1 to 50 $\mu$m, preferably less than 10 $\mu$m, for example from 1 to 10 $\mu$m, 1 to 5 $\mu$m or from 2 to 5 $\mu$m. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilised before filling into a suitable vial or ampoule and sealing.

Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof, are conventional formulations well known in the art, for example, as described in standard text books such as Harry's Cosmeticology published by Leonard Hill Books, Remington's Pharmaceutical Sciences, and the British and US Pharmacopoeias.

Suitably, the compound of formula (i), or if appropriate a pharmaceutically-acceptable salt thereof, will comprise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

When used herein the term "pharmaceutically-acceptable" encompasses materials suitable for both human and veterinary use.

The following Examples illustrate the invention.

Intermediate 1 N-Furfurylpropylamine

A solution of furfurylamine (1.0 g) in dry DMF (3 ml) was added to a cooled (0°–5° C.) stirred suspension of sodium hydride (60% dispersion; 0.46 g) in DMF (5 ml). After 15 minutes, a solution of 1-bromopropane (1.3 g) in dry DMF (2 ml) was added over 5 minutes. Stirring was continued for 1 h and the reaction mixture was then allowed to warm to room temperature and stirred overnight. The reaction was quenched by the addition of dilute hydrochloric acid. Aqueous sodium hydrogen carbonate solution (100 ml) was then added and the mixture was extracted with ethyl acetate (3×50 ml). The combined organic extracts were washed with water, brine and then dried (magnesium sulphate) and evaporated in vacuo. The residue was distilled under reduced pressure to furnish the title compound (0.21 g) as a colourless liquid.

Bp 85°–90° C./15 mmHg

Intermediate 2 2-Acetyl-4-bromo-7-methoxybenzofuran

A solution of bromine (5.5 ml) in methanol (100 ml) was added dropwise to a suspension of 2-acetyl-7-methoxybenzofuran (20 g) in methanol (300 ml) at 0° C. The ice bath was removed immediately and the mixture allowed to warm to room temperature. After 1 hour conversion was incomplete, so further bromine (0.75 ml) in methanol (25 ml) was added and the mixture stirred overnight. The reaction was quenched using aqueous sodium metabisulphite solution (300 ml) producing a precipitate that was filtered off and dried in vacuo to afford a brown solid (17.4 g).

TLC $R_f$ 0.90 (ethyl acetate)

Intermediate 3 2-Acetyl-7-methoxybenzofuran4-carboxylic acid

A mixture of Intermediate 2 (5 g), triphenylphosphine (98 mg), bis(triphenylphosphine)palladium (II) chloride (261 mg), triethylamine (2.85 ml) and water (1 ml) in tetrahyrofuran (25 ml) was purged with carbon monoxide gas in a Parr pressure reactor at 110 psi (758 kPa). This was heated to 110° C. (pressure now 220 psi=1517 kPa) and left for a week. On cooling and release of pressure the mixture was dissolved in 50% dichloromethane-water (200 ml) and taken to pH12 using aqueous sodium hydroxide(1M). The separated aqueous phase was acidified to pH1 using dilute hydrochloric acid(1M) and the resultant slurry extracted with dichloromethane (3×100 ml) then ethyl acetate (100 ml). These combined organic extracts were dried over magnesium sulphate, filtered and evaporated in vacuo to afford a yellow solid (2.58 g).

TLC $R_f$ 0.61 (ethyl acetate)

Intermediate 4 2-Acetyl-7-methoxybenzofuran-4-carbonyl chloride

Intermediate 3 (0.12 g) was suspended in anhydrous dichloromethane (4 ml) at room temperature under nitrogen and oxalyl chloride (0.1 ml) added followed by 3 drops of N,N-dimethylformamide. Evaporation in vacuo after 2 hours afforded the title compound as a yellow solid (~0.5 g).

TLC $R_f$ 0.60 (50%ethyl acetate in hexane)

Intermediate 5 2-Ethyl-7-methoxybenzofuran-4-carboxylic acid

2-Methyl-2-butene (9 g) was added to a solution of 2-ethyl-7-methoxybenzofurancarboxaldehyde (5 g) in 2-methyl-2-propanol (125 ml). A solution of sodium dihydrogen phosphate monohydrate (20.7 g) in water (15 ml) was added, followed by sodium chlorite (11.05 g). The resultant heterogeneous mixture was stirred vigorously for 30 minutes and then diluted with water (125 ml). The mixture was adjusted to pH 4 by the addition of 2M hydrochloric acid. The mixture was extracted with ethyl acetate (3×200 ml) and the combined organic extracts were washed with water (2×200 ml). The organic solution was concentrated to about 100 ml and then cooled to 10° C. The resultant precipitate was collected by filtration and dried at 500° C. in vacuo to afford a beige solid (4 g).

mp 215°–216° C.

Intermediate 6 4-Amino-3-chloropyridine

A solution of 4-aminopyridine (4.0 g) in concentrated hydrochloric acid (50 ml) was treated at 80°–85° C. with an aqueous solution of hydrogen peroxide (13.5% w/v). The solution was cooled to 0° C. After 30 minutes, the solution was carefully treated with an aqueous sodium hydroxide solution (50% w/v) maintaining the temperature below 15° C., The white solid produced was obtained by filtration and air dried to afford a white solid (4.9 g).

$R_f$ 0.36 (ethyl acetate).

mp 65°–67° C.

Intermediate 7 4-(Propylamino)pyridine

4-Aminopyridine (0.499 g) and propionaldehyde (0.5 g) in dichloromethane (50 ml) under an inert atmosphere were stirred at ambient temperature for 1.5 hours. Sodium triacetoxyborohydride (2.7 g) was added and left overnight. The reaction mixture was washed with aqueous sodium bicarbonate (2×40 ml) and extracted into dilute hydrochloric acid (2×40 ml). These acidic extracts were basified using potassium hydroxide pellets and extracted into dichloromethane (2×80 ml). The combined organic extracts were dried over anhydrous magnesium sulphate, filtered and evaporated in vacuo to yield an oily residue (0.11 g).

TLC $R_f$ 0.49 (10% methanol in ethyl acetate).

Intermediate 8 2-Ethyl-7-methoxy-4-N-(3-carboethoxyphenyl)benzofurancarboxamide

2-Ethyl-7-methoxybenzofuran-4-carbonyl chloride (1.0 g) was added to a solution of ethyl 3-aminobenzoate (0.72 g) in dichloromethane (30 ml) at room temperature under an inert atmosphere and the reaction mixture stirred at room temperature overnight. The mixture was poured into dilute aqueous hydrochloric acid and extracted with ethyl acetate (2×50 ml). The combined organic exacts were washed with water (50 ml), brine (50 ml), dried (magnesium sulphate) and evaporated in vacuo to yield the title compound (1.39 g) as a white solid mp 159°–161° C.

The following compound was prepared according to the above procedure.

Intermediate 9 2-Ethyl-7-methoxy-4-N-(4-carboethoxyphenyl)benzofurancarboxamide

Prepared from 2-ethyl-7-methoxybenzofuran-4-carbonyl chloride (1.3 g) and ethyl 4-aminobenzoate (1.0 g) to yield the title compound (0.76 g) as a white solid.

TLC $R_f$ 0.18 (25% ethyl acetate in hexane)

Intermediate 10 2-[1-(2,2-Dimethylpropyl)]-7-methoxybenzofuran

Sodium hydroxide (2.89 g) was added to a solution of o-vanillin (10 g) in ethanol (230 ml) at 40° C. After 10 minutes, 1-bromopinacolone (9.7 ml) was added and the resultant mixture was heated at 60° C. for 4 h then at reflux for a further 4 h.

The reaction mixture was cooled to room temperature and then concentrated in vacuo. The residue was partitioned between ethyl acetate (100 ml) and 0.2% aqueous sodium hydroxide solution (100 ml). The aqueous layer was extracted with ethyl acetate (2×75 ml) and the combined organic extracts were washed with water (100 ml) and brine (100 ml). The solution was dried (magnesium sulphate) and concentrated in vacuo to furnish 2-[1-(2,2-dimethyl-1-oxopropyl)]-7-methoxybenzofuran as a brown oil.

Hydrazine hydrate (3.2 ml) was added to a stirred suspension of 2-[1-(2,2-dimethyl-1-oxopropyl)]-7-methoxybenzofuran (3.0 g) in ethylene glycol (38 ml). The reaction mixture was heated to 65° C. for 1 h, then heated at reflux for 1.75 h to afford a yellow solution. After cooling to room temperature, water (50 ml) was added and the mixture extracted with dichloromethane (3×50 ml). The combined organic extracts were washed with 2M aqueous hydrochloric acid (15 ml), water (3×20 ml) and brine 50 ml). The solution was dried (magnesium sulphate) and concentrated in vacuo. Purification by column chromatography on silica, eluting with 5% ethyl acetate in hexane yielded the title compound (1.92 g) as a colourless oil.

TLC $R_f$ 0.35 (5% ethyl acetate in hexane)

Intermediate 11 2-[1-(2,2-Dimethylpropyl)]-7-methoxybenzofuran-4-carboxaldehyde

Phosphorus oxychloride (1.64 ml) was added dropwise to DMF (1 ml) at 0° C. under nitrogen and stirred for 10 minutes. A solution of 2-[1-(2,2-dimethylpropyl)]-7-methoxybenzofuran (1.92 g) in DMF (3.5 ml) was then added. A pale yellow solid formed and the reaction mixture was heated to 100° C. for 2 h. The reaction mixture was allowed to cool to room temperature overnight. A solution of 50% aqueous sodium acetate trihydrate (20 ml) was added cautiously and the resultant mixture was extracted with MTBE (3×25 ml). The combined organic phases were washed with water (2×20 ml), saturated aqueous sodium hydrogen carbonate solution (20 ml) and brine (30 ml). The solution was dried (magnesium sulphate) and concentrated in vacuo to provide the title compound (2.14 g) as a light brown oil.

TLC $R_f$ 0.25 (5% ethyl acetate in hexane)

Intermediate 12 2-[1(2,2-Dimethylpropyl)]-7-methoxybenzofuran-4-carboxylic acid

Prepared from Intermediate 11 (2.14 g), by the same procedure as for Intermediate 5. The title compound (1.81 g) was obtained as a pale yellow solid.

mp 173°–174° C.

EXAMPLE 1

2-Acetyl-7-methoxy-N-[3-pyridylmethyl]-4-benzofuransulphonamide

Triethylamine (0.43 ml) was added to a solution of 2-acetyl-7-methoxy-4-benzofuransulphonyl chloride (600 mg) and 3-(aminomethyl)pyridine (0.25 ml) in dichloromethane at room temperature. The resultant mixture was stirred for 20 hours and then diluted with dichloromethane (20 ml). The solution was washed with water (20 ml) and brine (20 ml) and dried (MgSO$_4$). Concentration in vacuo provided a dark oil which was applied to a silica column and eluted with 2% methanol in dichloromethane. The title compound was obtained as a pale yellow solid (161 mg). Mp 168°–170° C.

EXAMPLE 2

2-Acetyl-N-benzyl-7-methoxy-4-benzofuransulphonamide

Prepared from 2-acetyl-7-methoxy-4-benzofuransulphonyl chloride and benzylamine using the procedure of Example 1.

TLC $R_f$ 0.25 (30% ethyl acetate in hexane) Mp 158°–159° C.

EXAMPLE 3

2-Acetyl-N-furfuryl-7-methoxy-4-benzofuransulphonamide

Prepared using the procedure of Example 1. Trituration with diethyl ether afforded the title compound (0.33 g) as a white solid.

TLC $R_f$ 0.42 (50% ethyl acetate in hexane) Mp 182°–184° C.

EXAMPLE 4

2-Acetyl-N-furfuryl-N-propyl-7-methoxy-4-benzofuransulphonamide

Prepared from 2-acetyl-7-methoxy-4-benzofuransulphonyl chloride and Intermediate 1 using the procedure of Example 1. Purification by column chromatography on silica eluting with 5% ethyl acetate in dichloromethane gave the title compound (100 mg) as an off-white solid.

TLC $R_f$ 0.6 (5% ethyl acetate in dichloromethane) Mp 109°–111° C.

EXAMPLE 5

N-Benzyl-2ethyl-7-methoxy-4-benzofuransulphonamide

Hydrazine (6.96 g) was added to a suspension of Example 2 (10 g) in ethylene glygol (120 ml) at 38° C. The mixture was heated and potassium carbonate (7.7 g) was added at 65° C. Heating was continued until a temperature of 170° C. was attained. The mixture was cooled to room temperature and poured into a mixture of brine (300 ml), water (300 ml) and ethyl acetate (300 ml). The aqueous layer was extracted with ethyl acetate (2×300 ml) and the combined organic extracts were dried (MgSO$_4$) and concentrated in vacuo. The residue was applied to a silica column and eluted with 30% ethyl acetate in heptane to provide the title compound as an off-white solid (5.1 g).

TLC $R_f$ 0.13 (30% ethyl acetate in hexane)
Mp 105°–107° C.

The following compound was prepared using the above procedure:

EXAMPLE 6

2-Ethyl-7-methoxy-N-(3-pyridylmethyl)-4-benzofuransulphonamide

Purification by column chromatography on silica eluting with 1% triethylamine/10% methanol in ethyl acetate yielded the title compound as a pale yellow solid (0.36 g).

TLC $R_f$ 0.51 (10% methanol in ethyl acetate)
Mp 115°–117° C.

EXAMPLE 7

2-Acetyl-7-methoxy-N-(methanesulphonyl)-N-(3-pyridylmethyl)-4-benzofuransulphonamide A solution of Example 1 (126 mg) in dry DMF (2 ml) was cooled to 0° C. under nitrogen. Sodium hydride (60% dispersion in oil; 17 mg) was added and the mixture stirred for 15 minutes. Methanesulphonyl chloride (54 µl) was added and the resultant mixture was stirred at 0° C. for 1 hour and then at room temperature for 16 hours. Water (1 ml) was added and the mixture concentrated in vacuo. The residue was partitioned between water (10 ml) and dichloromethane (15 ml) and the layers separated. The aqueous phase was extracted with dichloromethane (2×5 ml) and the combined organic extracts were washed with brine (15 ml), dried (MgSO$_4$) and concentrated in vacuo. The residue was applied to a silica column and eluted with 2% methanol in dichloromethane. The titled compound was obtained as a pale yellow solid (48 mg).

TLC $R_f$ 0.15 (2% methanol in dichloromethane)
Mp 171°–172° C.

The following compounds were prepared using the above procedure.

EXAMPLE 8

N-Benzyl-2-ethyl-N-(methanesulphonyl)-7-methoxy-4-benzofuransulphonamide

This was prepared from Example 5.

TLC $R_f$ 0.75 (50% ethyl acetate in hexane)

IR (thin film) n$_{max}$ 1620, 1594, 1366, 1323, 1164, 1098 cm$^{-1}$

EXAMPLE 9

N-Benzyl-2-ethyl-7-methoxy-N-(2-pyridylmethyl)-4-benzofuransulphonamide

This was prepared as above using 2-(chloromethyl)pyridine.

TLC $R_f$ 0.38 (50% ethyl acetate in hexane)
IR (thin film) n$_{max}$ 1618, 1592, 1332, 1161, 1095 cm$^{-1}$

EXAMPLE 10

2-Ethyl-7-methoxy-N-(methanesulphonyl)-N-(3-pyridylmethyl)-4-benzofuransulphonamide This was prepared from Example 6. Purification by column chromatography eluting with 10% methanol in ethyl acetate afforded the title compound as a white foam (87 mg).

TLC $R_f$ 0.65 (10% methanol in ethyl acetate)
IR (thin film) n$_{max}$ 1575, 1405, 1290, 1164 cm$^{-1}$

EXAMPLE 11

2-Ethyl-7-methoxy-N-(methanesulphonyl)-N-(3-pyridylmethyl)-4-benzofuransulphonamide A solution of hydrogen chloride in ether (1M solution, 1.5 ml) was added to a solution of Example 10 (0.1 g) in dry dichloromethane (4 ml) under nitrogen. The resultant solution was stirred at room temperature for 90 minutes. Ether (10 ml) was added and the resultant precipitate was collected by filtration to provide the title compound as a cream-coloured solid (0.09 g).

Similarly prepared:

EXAMPLE 12

2-Acetyl-7-methoxy-N-(methanesulphonyl)-N-(3-pyridylmethyl)-4-benzofuransulphonamide hydrochloride From Example 7 (0.08 g) as a pale yellow solid (0.06 g).

EXAMPLE 13

2-Acetyl-7-methoxy-4-N-(3,5-dichloropyrid-4-yl)benzofurancarboxamide

Sodium hydride (0.03 g) was added to a solution of 4-amino-3,5-dichloropyridine (0.08 g) in anhydrous N,N-dimethylformamide (1 ml) at room temperature under nitrogen. This stirred mixture was warmed to 60° C. for 1 hour before addition of Intermediate 4 washed in with anhydrous N,N-dimethylformamide (2 ml). The brown mixture was heated at 60° C. for 4 hours, allowed to cool, poured into water (100 ml) and extracted into ethyl acetate (2×50 ml). These organic extracts were washed with water (50 ml) and saturated brine(50 ml) then dried over magnesium sulphate, filtered and evaporated in vacuo to give a crude residue (0.17 g). Purification by column chromatography on silica eluting with a 20–80% ethyl acetate in hexane gradient afforded a white solid (0.04 g).

TLC $R_f$ 0.20 (50% ethyl acetate in hexane)
mp 252°–254° C.

EXAMPLE 14

2-Ethyl-7-methoxy-4-N-(3,5-dichloropyrid-4-yl)benzofurancarboxamide

A suspension of Intermediate 5 (300 mg) in dry toluene (50 ml) under an inert atmosphere was treated with thionyl chloride (2 ml) and heated to reflux for 2 hours. The cooled reaction mixture was evaporated in vacuo and the residue azeotroped with dry toluene (2×10 ml) to afford the acid chloride as a white solid (325 mg).

4-Amino-3,5-dichloropyridine(230 mg) in dry N,N-dimethylformamide (20 ml) under an inert atmosphere was treated with sodium bis(trimethylsilyl)amine (1.5 ml; 1.0M in tetrahydrofuran) at ambient temperature for 30 minutes. The solid acid chloride (325 mg) was added to this mixture and heated at 50° C. for 3 hours then allowed to cool overnight. It was evaporated in vacuo, saturated aqueous sodium bicarbonate (50 ml) added and extracted into dichloromethane (2×50 ml). These extracts were dried over magnesium sulphate, filtered and evaporated in vacuo to give a crude residue. Purification by column chromatography on silica eluting with 50% ethyl acetate in hexane afforded a white solid (210 mg).

TLC $R_f$ 0.15 (25% ethyl acetate in hexane)
mp 199°–200° C.

EXAMPLE 15

2-Acetyl-7-methoxy-4-N-(pyrid-4-yl)benzofurancarboxamide

A solution of Intermediate 4 (164 mg) in anhydrous dichloromethane (10 ml) under nitrogen at 0° C., was treated with 4-aminopyridine (0.07 g), triethylamine (0. 12 g) and 4-dimethylaminopyridine (2 mg). This solution was allowed to warm to room temperature and stirred overnight. The reaction mixture was washed with saturated aqueous sodium bicarbonate (10 ml), water (10 ml) and saturated brine(10 ml) then dried over magnesium sulphate, filtered and evaporated in vacuo to give a crude residue. Purification by column chromatography on silica eluting with 5% methanol in dichoromethane afforded a pale yellow solid (85 mg).

TLC $R_f$ 0.27 (5% methanol in dichloromethane)
mp 247°–248° C. (dec)

EXAMPLE 16

2-Acetyl-7-methoxy-4-[N-(pyrid-4-yl)-N-propyl]benzofurancarboxamide

Intermediate 7 (0.08 g) was treated with Intermediate 4 (0.15 g) as in Example 15 to afford a pale yellow foam (129 mg).

TLC $R_f$ 0.57 (5% methanol in dichloromethane)
IR (film); 1292, 1587, 1647, 1685 cm$^{-1}$

EXAMPLE 17

2-Acetyl-7-methoxy-4N-(2-chlorophenyl)benzofurancarboxamide

2-Chloroaniline (0.42 ml) was treated with Intermediate 4 (1 g) as in Example 15. Purification by column chromatography on silica eluting with 50% ethyl acetate in hexane afforded a solid (137 mg).

mp 179°–181° C.

EXAMPLE 18

2-Acetyl-7-methoxy-4-N-2,6-dimethylphenyl)benzofurancarboxamide 2,6-Dimethylaniline (0.49 ml) was treated with Intermediate 4 (1 g) as in Example 15. Purification by column chromatography on silica eluting with 50% ethyl acetate in hexane afforded a solid (255 mg).

TLC $R_f$ 0.23 (50% ethyl acetate in hexane)
mp 225°–226° C.

EXAMPLE 19

2-Acetyl-7-methoxy-4-N-(4-methoxyphenyl)benzofurancarboxamide

4-Methoxyaniline (567 mg) was treated with Intermediate 4 (1.19 g) as in Example 15. Purification by column chromatography on silica eluting with 50% ethyl acetate in heptane afforded a yellow solid (103 mg).

TLC $R_f$ 0.26 (50% ethyl acetate in heptane)

EXAMPLE 20

2-Acetyl-7-methoxy-4-N-(3-bromo-5-methylpyrid-2-yl)benzofurancarboxamide

2-Amino-3-bromo-5-methylpyridine(0.64 g) in dry tetrahydrofuran (20 ml) was treated with sodium hydride (0.15 g; 60% dispersion in oil) under an inert atmosphere at ambient temperature for 15 minutes. A solution of Intermediate 4 (0.86 g) in dry tetrahydrofuran (10 ml) was added and then stirred overnight before evaporation in vacuo. Aqueous sodium bicarbonate (50 ml) was added and the mixture extracted with ethyl acetate (2×50 ml). These extracts were dried over magnesium sulphate, filtered and evaporated in vacuo. The crude residue was purified by column chromatography on silica eluting with 50% ethyl acetate in hexane to afford a pale yellow powder (95 mg).

TLC $R_f$ 0.5 (50% ethyl acetate in hexane)

EXAMPLE 21

2-Acetyl-7-methoxy-4-N-(3-methylphenyl)benzofurancarboxamide m-Toluidine (0.42 ml) was treated with Intermediate 4 (1 g) as in Example 15. Purification by column chromatography on silica eluting with 50% ethyl acetate in hexane afforded a yellow solid (200 mg).

TLC $R_f$ 0.5 (50% ethyl acetate in hexane)
mp 193°–195° C.

EXAMPLE 22

2-Acetyl-7-methoxy-4-N-(3,5-dichloropyrid-2- yl)benzofurancarboxamide

2-Amino3,5-dichloropyridine (0.758 g) was mated with Intermediate 4 (1.17 g) as in Example 13 using N,N- dimethylformamide as a cosolvent. Purification by column chromatography on silica eluting with 3% methanol in dichloromethane afforded a yellow solid (13 mg).

TLC $R_f$ 0.5 (50% ethyl acetate in hexane)

EXAMPLE 23

2-Acetyl-7-methoxy-4-N-(2-methylphenyl) benzofurancarboxamide

2-Methylaniline (0.21 ml) was treated with Intermediate 4 (0.5 g) as in Example 15. Purification by column chromatography on silica eluting with 50% ethyl acetate in hexane afforded a yellow solid (128 mg).

TLC $R_f$ 0.24 (50% ethyl acetate in hexane)
mp 174°–175° C.

EXAMPLE 24

2-Acetyl-7-methoxy-4-N-(4-methoxy-2-methylphenyl)benzofurancarboxamide

4-Methoxy-2-methylaniline (0.56 ml) was treated with Intermediate 4 (10 g) as in Example 15. Purification by column chromatography on silica eluting with 50% ethyl acetate in hexane afforded a yellow solid (235 mg).

TLC $R_f$ 0.25 (50% ethyl acetate in hexane)
mp 217°–218° C.

EXAMPLE 25

2-Acetyl-7-methoxy-4-N-(pyrimidin-4-yl) benzofurancarboxamide

4-Aminopyridine (0.376 g) was treated with Intermediate 4 (1 g) as in Example 15. Purification by column chromatography on silica eluting with a 0–10% methanol in ethyl acetate gradient afforded a yellow solid (0.14 g).

TLC $R_f$ 0.49 (10% methanol in ethyl acetate)
mp 212°–214° C.

EXAMPLE 26

2-Acetyl-7-methoxy-4-N-(2-trifluoromethylphenyl) benzofurancarboxamide

2-Aminobenzotrifluoride (0.5 ml) was treated with Intermediate 4 (1.0 g) as in Example 15. Purification by column chromatography on silica eluting with 50% ethyl acetate in hexane afforded a yellow solid (0.12 g).

mp 164°–166° C.

EXAMPLE 27

2-Acetyl-7-methoxy-4-N-[2-(piperidin-1-yl)phenyl] benzofurancarboxamide

N-(2-Aminophenyl)piperidine (700 mg) was treated with Intermediate 4 (1.0 g) as in Example 15. Purification by column chromatography on silica eluting with 40% ethyl acetate in hexane afforded a yellow solid (300 mg), TLC $R_f$ 0.5 (50% ethyl acetate in hexane)
mp 170°–171° C.

EXAMPLE 28

2-Acetyl-7-methoxy-4-N-(3-chloropyrid-4-yl) benzofurancarboxamide

Intermediate 6 (0.26 g) was treated with Intermediate 4 (0.5 g) as in Example 13, except that the initial anion generation was performed at ambient temperature and using 15-crown-5 (0.90 g). Purification by column chromatography on silica eluting with 5% methanol in dichloromethane afforded an off-white solid (0.08 g).

TLC $R_f$ 0.65 (5% methanol in dichloromethane)
mp 197°–200° C.

EXAMPLE 29

2-Acetyl-7-methoxy-4-N-(2-trifluoromethoxyphenyl)benzofurancarboxamide

2-Trifluoromethoxyaniline (0.49 g) was treated with Intermediate 4 (0.7 g) as in Example 15. Purification by column chromatography on silica eluting with 50% ethyl acetate in hexane afforded a yellow solid (0.065 g).

TLC $R_f$ 0.49 (50% ethyl acetate in hexane)
mp 163°–165° C.

EXAMPLE 30

2-Acetyl-7-methoxy-4-N-2-ethylphenyl) benzofurancarboxamide

2-Ethylaniline (0.48 g) was treated with Intermediate 4 (1.0 g) as in Example 15. Purification by column chromatography on silica eluting with 25% ethyl acetate in hexane afforded an off-white solid (310 mg).

TLC $R_f$ 0.13 (25% ethyl acetate in hexane)
mp 174°–175° C.

EXAMPLE 31

2-Acetyl-7-methoxy-4-N-(2-biphenyl) benzofurancarboxamide

2-Aminobiphenyl (0.5 g) was treated with Intermediate 4 (0.73 g) as in Example 15. Purification by column chromatography on silica eluting with 5% methanol in dichloromethane then trituration with diethyl ether afforded a cream solid (0.17 g).

TLC $R_f$ 0.5 (50% ethyl acetate in hexane)
mp 131°–133° C.

EXAMPLE 32

2-Acetyl-7-methoxy-4-N-(3-methylpyrid-2-yl) benzofurancarboxamide

2-Amino-3-picoline (0.32 ml) was treated with Intermediate 4 (0.73 g) as in Example 15. Purification by column chromatography on silica eluting with 5% methanol in dichloromethane afforded a yellow solid (0.12 g).

TLC $R_f$ 0.40 (5% methanol in dichloromethane)

EXAMPLE 33

2-Ethyl-7-methoxy-4-N-(2-chloropyrid-3-yl) benzofurancarboxamide

3-Amino-2-chloropyridine (0.88 g) was treated with Intermediate 4 (1.8 g) as in Example 13 except that the anion generation was performed at ambient temperature for 1.5 hours. Purification by flash chromatography on silica eluting with hot ethyl acetate then trituration with diethyl ether afforded a beige solid (0.53 g)

TLC $R_f$ 0.35 (50% ethyl acetate in hexane)
mp 124°–125° C.

EXAMPLE 34

2-Acetyl-7-methoxy-4-N-(2-methoxyphenyl)benzofuran-carboxamide o-Anisidine (0.49 g) was treated with Intermediate 4 (1 g) as in Example 15. Purification by column chromatography on silica eluting with 30% ethyl acetate in hexane afforded a yellow solid (160 mg).

EXAMPLE 35

2-Acetyl-7-methoxy-4-N-(2-chloropyrid-3-yl)benzofurancarboxamide

3-Amino-2-chloropyridine (509 mg) was treated with Intermediate 4 (1.0 g) as in Example 13. Purification by column chromatography on silica eluting with 25% ethyl acetate in hexane afforded a yellow solid (205 mg).

EXAMPLE 36

2-Acetyl-7-methoxy-4-N-(2-chloro-6-methylphenyl)benzofurancarboxamide

2-Chloro-6-methylaniline (0.56 g) was treated with Intermediate 4 (1 g) as in Example 15. Purification by recrystallisation from dichloromethane afforded a brown solid (160 mg).

TLC $R_f$ 0.4 (5% methanol in dichloromethane)

EXAMPLE 37

2-(2-Hydroxyethyl)-7-methoxy-4-N-(3,5-dichloropyrid-4-yl)benzofurancarboxamide Example 13 (0.50 g) was suspended in dry methanol (20 ml) and treated with sodium borohydride (196 mg) at ambient temperature. Some external ice cooling was required then stirred overnight. The reaction mixture was poured into water and extracted into ethyl acetate. Evaporation in vacuo yielded a solid that was purified by column chromatography using 5% methanol in dichloromethane to afford a white solid (400 mg).

TLC $R_f$ 0.52 (80% ethyl acetate in heptane)
mp 229°–231° C.

EXAMPLE 38

2-(3-Pyrid-3-yl-1-oxopropyl)-7-methoxy-4-N-(3,5-dichloropyrid-4-yl)benzofurancarboxamide A solution of Example 13 (0.40 g) in dry N,N-dimethylformamide (5 ml) under an inert atmosphere was cooled to −10° C. and sodium hydride (60% dispersion in oil, 0.11 g) was added over 30 minutes. After 1 hour at −1° C., 3-picolyl chloride hydrochloride (0.20 g) was added and the mixture stirred for a further 2 hours before allowing to warm to room temperature overnight. It was poured into water and extracted into ethyl acetate. These extracts were washed with water and saturated brine then dried over anhydrous magnesium sulphate, filtered and evaporated in vacuo. The resultant residue was purified by column chromatography using a 3–10% methanol in dichloromethane gradient then triturated with diethyl ether to yield a beige powder (15.5 mg).

TLC $R_f$ 0.27 (10% methanol in dichloromethane).

EXAMPLE 39

2-(1-Benzyloxyimino)ethyl-7-methoxy-4-N-(3,5-dichloropyrid-4-yl)benzofurancarboxamide Example 13 (100 mg) was refluxed under Dean-Stark conditions in dry toluene (40 ml) with dry pyridine (64 μl) and O-benzylhydroxylamine hydrochloride (126 mg) under an inert atmosphere. After 2 hours the mixture was allowed to cool and left stirring overnight. Addition of methanol and acetone formed a precipitate. This was filtered off to afford a solid (26 mg).

TLC $R_f$ 0.45 (50% ethyl acetate in hexane).

EXAMPLE 40

2-Ethyl-7-methoxy-4-N-(3-carboxyphenyl)benzofurancarboxamide

A solution of Intermediate 8 (0.78 g) in THF (25 ml) was treated with a solution of lithium hydroxide monohydrate (0.18 g) in water (25 ml) and the reaction mixture stirred at room temperature overnight. The reaction mixture was concentrated in vacuo, diluted with water (100 ml) and acidified with dilute aqueous hydrochloric acid. The resulting white precipitate was collected, washed with water and dried in vacuo to afford the title compound (0.68 g) as a white solid.

TLC $R_f$ 0.35 (5% methanol in dichloromethane)
mp 265°–267° C.

The following compound was prepared according to the above procedure.

EXAMPLE 41

2-Ethyl-7-methoxy-4-N-(4-carboxyphenyl)benzofurancarboxamide

Prepared from Intermediate 9 (0.67 g) to afford the title compound (0.59 g) as a white solid.

TLC $R_f$ 0.4 (5% methanol in dichloromethane)
mp 279°–280° C.

EXAMPLE 42

2-[1-(2,2-Dimethylpropyl)]-7-methoxy-4-N-(3,5-dichloropyrid-4-yl)benzofurancarboxamide Thionyl chloride (1.65 ml) was added to a suspension of Intermediate 12 (0.59 g) in toluene (10 ml) and the mixture heated at reflux for 3 h. The mixture was 10 stirred at room temperature overnight and concentrated in vacuo. The residue was azeotroped several times with toluene to furnish 2-[1-(2,2-dimethylpropyl)]-7-methoxybenzofuran-4-carbonyl chloride (0.63 g).

Sodium hexamethyldisilazide (1M solution in THF, 4.5 ml) was added to a solution of 4-amino-3,5-dichloroaminopyridine (0.74 g) in dry DMF (2 ml) at room temperature under nitrogen. The mixture was stirred at room temperature for 0.5 h, then warmed to 50° C. A solution of 2-[1-(2,2-dimethylpropyl)]-7-methoxybenzofuran-4-carbonyl chloride (0.63 g) in DMF was added and the reaction mixture stirred for a further 3 h, then at room temperature for 16 h. Water (20 ml) was added and the resultant precipitate was collected and dried in vacuo. Purification by column chromatography on silica, eluting with 25% ethyl acetate in hexane afforded the title compound (0.29 g) as a pale yellow solid.

TLC $R_f$ 0.4 (50% ethyl acetate in hexane)
mp 164°–165° C.

Assay methods

The assays used to confirm the phosphodiesterase IV inhibitory activity of compounds of formula (i) are standard assay procedures as disclosed by Schilling et al, Anal. Biochem. 216:154 (1994), Thompson and Strada, Adv. Cycl.

Nucl. Res. 8:119 (1979) and Gristwood and Owen, Br. J. Pharmacol. 87:91P (1986).

Compounds of formula (i) have exhibited activity at levels consistent with those believed to be useful in treating phosphodiesterase IV-related disease states in those assays.

The ability of compounds of formula (i) to inhibit TNF production in human monocytes is measured as follows. Peripheral blood mononuclear cells are prepared from freshly taken blood by standard procedures. Cells are plated out in RPMI1640+1% foetal calf serum in the presence and absence of inhibitors. LPS (100 ng/ml) is added and cultures are incubated for 22 h at 37° C. in an atmosphere of 95% air/5% $CO_2$. Supernatants are tested for TNFα by ELISA using commercially available kits.

In vivo activity in a skin eosinophilia model is determined by using the methods described by Hellewell et al, Br, J. Pharmacol, 111:811 (1994) and Br, J. Pharmacol, 110:416 (1993). Activity in a lung model is measured using the procedures described by Kallos and Kallos, Int, Archs. Allergy Appl. Immunol. 73:77 (1984), and Sanjar et al, Br. J. Pharmacol, 99:679 (1990).

An additional lung model, which allows measurement of inhibition of the early and late-phase asthmatic responses and also the inhibition of airway hypereactivity, is described by Broadley et at, Pulmonary Pharmacol. 7:311 (1994), J. Immunological Methods 190:51 (1996) and British J. Pharmacol. 116:2351 (1995). Compounds of the invention show activity in this model.

We claim:

1. A compound having the following formula:

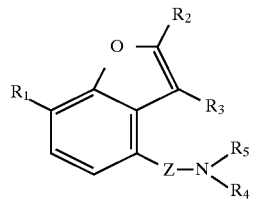

wherein Z is $SO_2$,
- $R_1$ represents alkoxy optionally substituted with one or more halogens, OH or thioalkyl;
- $R_2$ and $R_3$ are the same or different and are each selected from the group consisting of H, $R_6$, $COR_6$, $C(=NOR_{11})R_6$, CN, $CO_2H$, $CO_2R_{10}$, $CONH_2$, $CONHR_6$ and $CON(R_6)_2$;
- $R_4$ is selected from the group consisting of H, arylalkyl, heteroarylalkyl, heterocycloalkyl, $S(O)_m R_{10}$ and alkyl optionally substituted with one or more substituents selected from the group consisting of hydroxy, alkoxy, $CO_2R_7$, $SO_2NR_{11}R_{12}$, $CONR_{11}R_{12}$, CN, carbonyl oxygen, $NR_8R_9$, $COR_{10}$ and $S(O)_n R_{10}$;
- $R_5$ is selected from the group consisting of aryl, heteroaryl, heterocyclo, arylalkyl, heteroarylalkyl and heterocycloalkyl;
- in $R_4$ and/or $R_5$ the aryl/heteroaryl/heterocyclo portion is optionally substituted with one or more substituents alkyl-$R_{13}$ or $R_{13}$;
- $R_6$ represents $R_{10}$ optionally substituted at any position with $R_{14}$;
- $R_7$ is selected from the group consisting of alkyl, arylalkyl, heteroarylalkyl, and heterocycloalkyl;
- $R_8$ is selected from a group consisting of H, aryl, heteroaryl, heterocyclo, alkyl, arylalkyl, heteroarylalkyl, heterocycloalkyl, alkylcarbonyl, alkoxycarbonyl, arylsulphonyl, heteroarylsulphonyl, heterocyclosulphonyl, arylcarbonyl, heteroarylcarbonyl, heterocyclocarbonyl and alkylsulphonyl;
- $R_{10}$ is selected from a group consisting of alkyl, cycloalkyl, aryl, heteroaryl, heterocyclo, arylalkyl, heteroarylalkyl and heterocycloalkyl;
- $R_9$, $R_{11}$ and $R_{12}$ are the same or different and are each H or $R_{10}$;
- $R_{13}$ is selected from the group consisting of H, aryl, heteroaryl, heterocyclo, hydroxy, alkoxy, aryloxy, heteroaryloxy, heterocyclooxy, arylalkyloxy, heteroarylalkyloxy, heterocycloalkyloxy, $CO_2R_7$, $CONR_{11}R_{12}$, $SO_2NR_{11}R_{12}$, halogen, —CN, —$NR_8R_9$, $COR_{10}$, $S(O)_n R_{10}$ and carbonyl oxygen;
- $R_{14}$ is selected from the group consisting of OH, carbonyl oxygen, $OR_{10}$, $NR_8R_9$, CN, $CO_2H$, $CO_2R_{10}$, $CONR_{11}R_{12}$ and $COR_{10}$;
- m is an integer of up to 2; and
- n represents 0–2;

or a pharmaceutically-acceptable salt thereof.

2. The compound of claim 1, wherein
- $R_1$ is $C_{1-3}$ alkoxy optionally substituted by one or more halogens;
- $R_2$ and $R_3$ are each independently selected from the group consisting of H, CN, $CO_2H$, $C_{1-6}$ alkyl esters thereof, $C_{1-6}$ alkyl amides thereof, and alkyl optionally substituted with one or more substituents selected from the group consisting of carbonyl oxygen, hydroxy, alkoxy, aryloxy, arylalkoxy, alkylamino, arylalkylamino or arylamino, and cycloalkyl optionally substituted with one or more substituents selected from the group consisting of carbonyl oxygen, hydroxy, $C_{1-6}$ alkoxy, aryloxy, aryalkyloxy, $C_{1-6}$ alkylamino, arylalkylamino or arylamino;
- $R_4$ is selected from the group consisting of H, arylalkyl, heteroarylalkyl, $S(O)_m R_{10}$, alkyl optionally substituted with carbonyl oxygen, $NR_8R_9$, $S(O)_n R_{10}$, $COR_{10}$, hydroxy, $C_{1-6}$ alkoxycarbonyl, $C_{1-6}$ alkylaminocarbonyl and CN;
- $R_5$ is selected from the group consisting of arylalkyl and heteroarylalkyl;
- $R_8$ is selected from a group consisting of H, alkyl, alkylcarbonyl, alkoxycarbonyl, arylsulphonyl, arylcarbonyl and alkylsulphonyl;
- $R_9$ represents H or alkyl; and
- $R_{10}$ is selected from a group consisting of alkyl, aryalkyl and heteroarylalkyl.

3. The compound of claim 1, wherein
- $R_2$ and $R_3$ are each independently selected from the group consisting of H, $R_6$ and $COR_6$; and
- $R_6$ is selected from the group consisting of alkyl, aryl, heteroaryl, heterocyclo, arylalkyl, heteroarylalkyl and heterocycloalkyl.

4. The compound of claim 1, selected from
2-acetyl-N-benzyl-7-methoxy-4-benzofuransulphonamide,
N-benzyl-2-ethyl-7-methoxy-4-benzofuransulphonamide,
2-acetyl-7-methoxy-N-(methanesulphonyl)-N-(3-pyridylmethyl)-4-benzofuransulphonamide,
N-benzyl-2-ethyl-N-(methanesulphonyl)-7-methoxy-4-benzofuransulphonamide, and
N-benzyl-2-ethyl-7-methoxy-N-(2-pyridylmethyl)-4-benzofuransulphonamide.

5. The compound of claim 1, selected from 2-acetyl-N-furfuryl-7-methoxy-4-benzofuransulphonamide, 2-acetyl-N-furfuryl-N-propyl-7-methoxy-4-benzofuransulphonamide, 2-ethyl-7-methoxy-N-(3-pyridylmethyl)-4-benzofuransulphonamide, and 2-ethyl-7-methoxy-N-(methanesulphonyl)-N-(3-pyridylmethyl)-4-benzofuransulphonamide.

6. The compound of claim 1, selected from the group consisting of 2-ethyl-7-methoxy-N-methanesulphonyl)-N-(3-pyridylmethyl)-4-benzofuransulphonamide hydrochloride and 2-acetyl-7-methoxy-N-(methanesulphonyl)-N-(3-pyridylmethyl)-4-benzofuransulphonamide hydrochloride.

7. The compound of claim 1, in the form of an enantiomer or mixture of enantiomers.

8. A pharmaceutical composition for therapeutic use comprising a compound of claim 1 and a pharmaceutically-acceptable carrier or excipient.

9. A method for treating a human or animal hosting or susceptible to hosting a disease state capable of being modulated by inhibition of phosphodiesterase IV or Tumour Necrosis Factor which comprises treating said human or animal with an effective amount of a compound of claim 1 or a pharmaceutically-acceptable salt thereof.

10. The method, according to claim 9, wherein said disease state is a pathological condition associated with a function of phosphodiesterase IV, eosinophil accumulation, or a function of the eosinophil.

11. The method, according to claim 10, wherein the pathological condition is selected from the group consisting of asthma, chronic bronchitis, atopic dermatitis, urticaria, allergic rhinitis, allergic conjunctivitis, vernal conjunctivitis, inflammation of the eye, allergic responses in the eye, eosinophilic granuloma, psoriasis, rheumatoid arthritis, gouty arthritis and other arthritic conditions, ulcerative colitis, Crohn's disease, adult respiratory distress syndrome, diabetes insipidus, keratosis, atopic eczema, atopic dermatitis, cerebral senility, multi-infarct dementia, senile dementia, memory impairment associated with Parkinson's disease, depression, cardiac arrest, stroke and intermittent claudication.

12. The method, according to claim 10, wherein the pathological condition is selected from the group consisting of chronic bronchitis, allergic rhinitis, and adult respiratory distress syndrome.

13. The method, according to claim 9, wherein the disease state is capable of being modulated by TNF inhibition.

14. The method, according to claim 13, wherein the disease state is selected from the group consisting of inflammatory disease and autoimmune disease.

15. The method, according to claim 14, wherein the disease state is selected from the group consisting of joint inflammation, arthritis, rheumatoid arthritis, rheumatoid spondylitis and osteoarthritis, sepsis, septic shock, endotoxic shock, gram negative sepsis, toxic shock syndrome, acute respiratory distress syndrome, cerebral malaria, chronic pulmonary inflammatory disease, pulmonary sarcoidosis, asthma, bone resorption diseases, reperfusion injury, graft vs host reaction, allograft rejection, malaria, myalgias, HIV, AIDS, ARC, cachexia, Crohn's disease, ulcerative colitis, pyresis, systemic lupus erythematosus, multiple sclerosis, type 1 diabetes mellitus, psoriasis, Bechet's disease, anaphylactoid purpura nephritis, chronic glomerulonephritis, inflammatory bowel disease and leukemia.

16. The method, according to claim 11, wherein the pathological condition is asthma.

17. The method, according to claim 15, wherein the disease state is asthma.

18. The method, according to claim 15, wherein the disease state is selected from the group consisting of acute respiratory distress syndrome, pulmonary inflammatory disease and pulmonary sarcoidosis.

19. The method, according to claim 15, wherein the disease state is joint inflammation.

20. The method according to claim 10, wherein the disease state is tardive dyskinesia.

21. The method, according to claim 14, wherein the disease state is tardive dyskinesia.

22. The method, according to claim 13, wherein the disease state is selected from the group consisting of a yeast infection and a fungal infection.

23. A method for providing gastroprotection for a human or animal in need of such treatment, comprising treating said human or animal with an effective amount of a compound of claim 1.

24. A method for treating a human or animal having or susceptible to having a neurogenic inflammatory disease associated with irritation and pain, comprising treating said human or animal with an effective amount of a compound of claim 1.

25. A composition selected from the group consisting of analgesics, anti-tussives and anti-hyperalgesics wherein said composition comprises a compound of claim 1 and a pharmaceutically-acceptable carrier or excipient.

* * * * *